Figure 1:
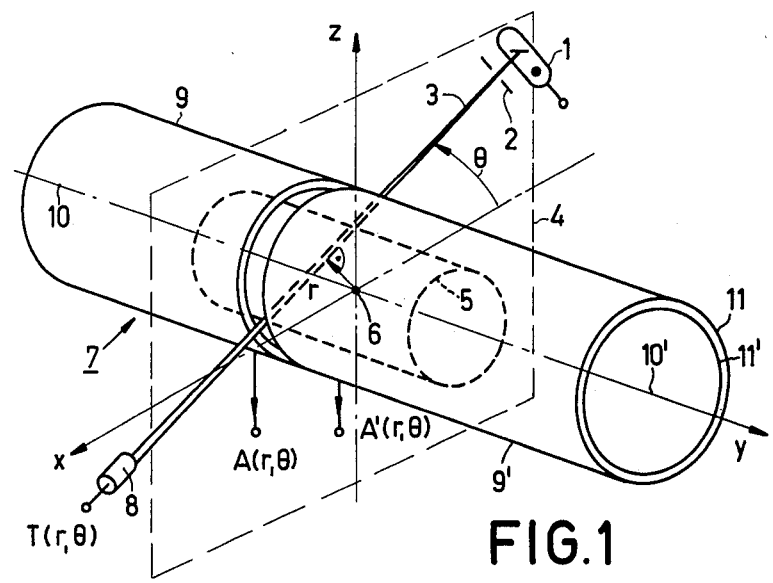

United States Patent [19]

Harding

[11] 4,277,686

[45] Jul. 7, 1981

[54] DEVICE FOR DETERMINING INTERNAL BODY STRUCTURES BY MEANS OF SCATTERED RADIATION

[75] Inventor: Geoffrey Harding, Rellingen, Fed. Rep. of Germany

[73] Assignee: U.S. Philips Corporation, New York, N.Y.

[21] Appl. No.: 56,479

[22] Filed: Jul. 11, 1979

[30] Foreign Application Priority Data

Jul. 17, 1978 [DE] Fed. Rep. of Germany ....... 2831311

[51] Int. Cl.$^3$ ................................................ A61B 6/00
[52] U.S. Cl. ................................. 250/445 T; 250/369
[58] Field of Search ..................... 250/320, 369, 445 T

[56] References Cited

U.S. PATENT DOCUMENTS

| | | | |
|---|---|---|---|
| 4,124,804 | 11/1978 | Mirell | 250/445 T |
| 4,149,080 | 4/1979 | Schittenhelm | 250/445 T |

Primary Examiner—Davis L. Willis
Assistant Examiner—T. N. Grigsby
Attorney, Agent, or Firm—Thomas A. Briody; Robert T. Mayer; Paul R. Miller

[57] ABSTRACT

The invention relates to a device for measuring a scatter coefficient distribution in a plane of a body. The plane is irradiated in different directions by a primary radiation beam along beam paths which are each time situated in parallel in a direction. Scattered radiation which is generated by a primary radiation beam along its path is measured by detectors which are situated on both sides of the plane and which enclose the body as completely as possible. The scatter coefficient distribution is determined by iteration by calculating a scatter value for each beam path from an assumed distribution and by comparing this scatter value with the associated measured scattered radiation. From the difference between calculated and measured values a correction is determined and taken up in the calculated value.

5 Claims, 3 Drawing Figures

DEVICE FOR DETERMINING INTERNAL BODY STRUCTURES BY MEANS OF SCATTERED RADIATION

The invention relates to a device for determining the internal structure of a flat examination zone of a body, comprising a radiation source which emits a primary radiation beam which extends in the plane of the examination zone and which has a small cross-section, the source being displaceable in a direction which extends in the plane, transversely of the direction of the primary radiation beam, and also being rotatable around an axis extending perpendicularly to the plane, comprising a detector device for generating measuring signals by the detection of the radiation emerging from the body, and also comprising a computer and display device for calculating, from the measuring signals, and for displaying the internal structure.

A device of this kind is already known from German Auslegeschrift No. 19 41 433. This device comprises an X-ray source or gamma radiation source which emits a primary radiation beam having a small cross-section which irradiates a flat examination zone of a body in different directions, situated in the plane, each time along radiation paths which are situated in parallel in one direction. The primary radiation beam is detected by means of a detector for generating transmission signals. Using a computer, the distribution of the absorption or transmission coefficients of the irradiated slice of the body is calculated from the transmission signals.

To this end, the irradiated slice of the body is imagined to be divided into a matrix of elements, an absorption or transmission coefficient being displayed in each element.

However, in the body the primary radiation beam is substantially attenuated along its radiation paths by absorption and scattering. The ratio of the intensity before and after the passage through the body, therefore, is comparatively large. Because the accuracy of the reconstruction, however, is dependent of the intensity of the primary radiation beam after the passage through the body, the intensity of radiation must be comparatively high prior to the passage through the body, so that a high radiation load for the body occurs.

The invention has for its object to provide a device which enables determination of the internal structure of a body with a comparatively low radiation load for the body.

To this end, a device in accordance with the invention is characterized in that the detector device is not struck by the primary radiation beam and is situated at least on one side of the plane in order to detect scattered radiation generated by a primary radiation beam along its beam path so that a scatter signal is obtained which is associated with the beam path, the detector device at least partly enclosing the body, and the computer calculating a distribution of the scatter coefficients in the irradiated plane on the basis of the scatter signals obtained.

Primary beams of X-rays or gamma rays in the energy range of from one hundred to a few hundreds of kilo-electronvolts (keV) are attenuated by incoherent scattering (Compton scattering) during irradiation of a body. When a human body is examined, the photoelectric absorption occurring in the body can be neglected for radiation energies of approximately 150 keV. In the field of examination of materials, the photoelectric absorption can be neglected for radiation energies of some hundreds of keV, depending on the nature of the material to be examined.

On the basis of the comparatively high attenuation encountered by the primary radiation beam during its passage through a body, the ratio of the intensity before and after the passage through the body is very large, while the ratio of scattered and incident radiation is substantially larger. The relative inaccuracies ($\partial I_t/I_t$ and $\partial I_s/I_s$) with which the intensity of the radiation behind the body ($I_t$) and the intensity ($I_s$) of the scattered radiation, respectively, is measured and which influence the quality of the reconstructed structure distribution are inversely proportional to the root of the intensity of the transmitted and scattered radiation, respectively. Thus, the relative inaccuracy of the intensity of the transmitted radiation is much higher than that of the intensity of the scattered radiation. By measurement of the scattered radiation it can be achieved that the reconstruction of a scatter coefficient distribution can be performed with the same accuracy as the reconstruction of an absorption coefficient distribution obtained from measurements of the transmitted radiation, but already with a much lower intensity of the incident primary radiation beam, so that the radiation load for the body is substantially reduced.

The scatter signals are then measured by measurement of an as large as possible part of the scattered radiation generated by the primary radiation beam along a beam path. For this it is necessary that the detector device envelops the body to be examined as completely as possible. From the scattered radiation signals obtained, the distribution can be calculated of scatter coefficients which represent the attenuation of the radiation on the basis of the scattering at elements of a matrix which is permanently associated with the body. The indivdual scatter coefficients at the matrix elements can then be converted into corresponding grey values for the display of individual slice images and can be made visible, for example, on an image matrix (monitor) or on a printer.

In a further attractive embodiment of the invention, the detector device comprises two identical, hollow-cylinder detectors which together substantially completely envelop the body and which are arranged at a distance from each other in a mirror-inverted manner with respect to the plane, cylinder axes of the cylinder detectors being coincident and extending transversely of the plane.

By means of such a measuring arrangement it is achieved that the scattered radiation which is emitted at a larger angle with respect to the radiation direction of the primary radiation beam is also measured, so that the scattered radiation generated is substantially completely detected and the accuracy of the reconstructed scatter coefficient distribution is improved.

The output signals generated by means of the two hollow-cylinder detectors, being a measure for the scattered radiation generated by the primary radiation beam, are added in order to determine a scatter signal. To this end, the hollow cylinder detectors are connected to an adding stage for the adding of their output signals.

In a further embodiment of the invention, the hollow-cylinder detectors form an integral unit and are rotatable about their cylinder axis and displaceable in a direction perpendicular to the cylinder axis, the cylinder detectors being provided with apertures for passage of primary radiation beam which are situated in the plane and radially opposite each other. A cylinder detector of this kind also enables measurement of scattered radiation occurring in the plane, so that only a very small part of the total scattered radiation generated is not detected. In the extreme case, the scattered radiation emitted in the direction of the cylinder axis can also be measured if one of the outer end faces of the hollow-cylinder detectors is covered with detector plates.

In an attractive further embodiment of a device in accordance with the invention, moreover, a detector for detecting the primary radiation beam is arranged in the plane. Besides the measurement of the scattered radiation generated by the primary radiation beam along its beam path, the radiation of the primary radiation beam which is transmitted by the body is also measured for generating transmission signals. It is thus achieved that also in an energy range of the radiation of the primary radiation beam in which the photoelectric absorption can no longer be neglected, a distribution of the scatter coefficient can be reconstructed by a combination of transmission signals and scatter signals while the radiation load for the body is reduced.

Figure 2:
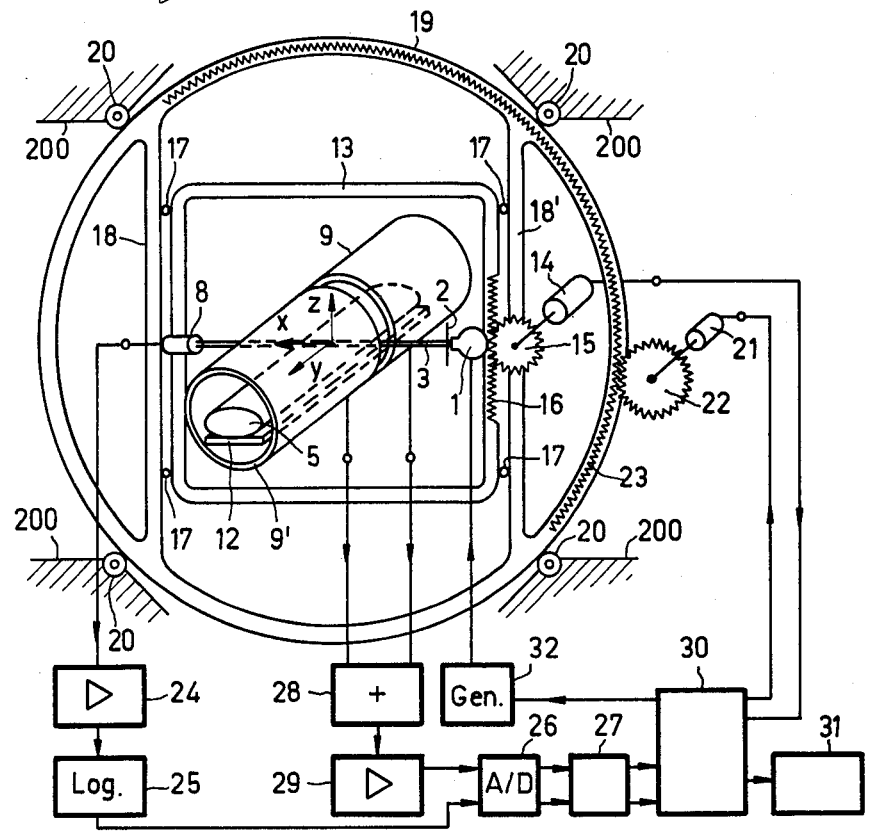
Figure 3:
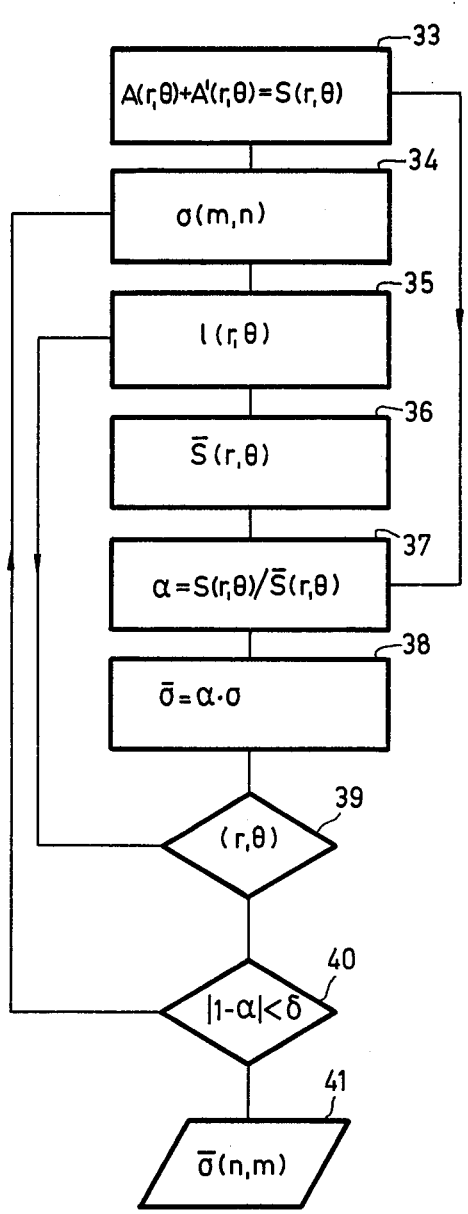

An embodiment of the device in accordance with the invention will be described in detail hereinafter with reference to the accompanying diagrammatic drawing:

FIG. 1 shows a detector device for measuring the scattered radiation and a further detector for measuring the transmitted radiation, FIG. 2 shows a device in accordance with the invention with the detector device and the further detector and FIG. 3 shows a process diagram of a method of determining a scatter coefficient distribution.

FIG. 1 shows an X-ray source 1 which emits a thin primary radiation beam 3 which is collimated by an aperture 2 and which extends in the X-Z plane of a Carthesian system of coordinates XYZ. The primary radiation beam 3 has a small angle of aperture (not shown). The beam path $l(r, \theta)$ of the radiation is defined by the distance r from the origin 6 of the system of coordinates and the angle $\theta$ enclosed by the path and the X-axis, viewed from the source 1. A body 5 to be examined which extends in a direction perpendicular to the plane 4 (y-axis) is irradiated by the primary radiation beam 3 in different directions $\theta$ situated in the plane 4, each direction $\theta$ in parallel beam paths $l(r, \theta)$, for which each time a different distance r is adjusted. The position of the primary radiation beam 3 is changed by displacement or rotation of the X-ray source 1 in the plane 4 (to be described with reference to FIG. 2), so that a flat examination zone of the body 5, which may be for example, a human body, can be scanned. The position of the body 5 or the hollow-cylinder detectors 9 and 9' is not changed.

The scattered radiation emerging from the body 5 and generated by the primary radiation beam 3 is detected by a detector device 7 which consists of two hollow-cylinder detectors 9 and 9' which have the same shape and which are arranged in a mirror-inverted manner on both sides of the plane 4 so that their cylinder axes 10 and 10' (y-axis) extend perpendicularly through the plane 4 and are coincident. Both hollow-cylinder detectors 9 and 9' are removed from each other only so far that they just fail to impede the primary radiation beam 3 passing therebetween. The two cylinder detectors 9 and 9' measure the major part of the scattered radiation each time generated by the primary radiation beam 3 in a beam path $l(r, \theta)$. The individual hollow-cylinder detectors 9 and 9' produce output signals $A(r, \theta)$ and $A'(r, \theta)$ which correspond to the measured scattered radiation and which are added in order to form a scatter signal $S(r, \theta)$. (FIG. 2). There is also provided a detector 8 which is arranged in the plane 4 and which measured the transmitted radiation of the primary radiation beam 3 in order to generate transmission signals $T(r, \theta)$.

From the scatter signals $S(r, \theta)$ obtained for all beam paths $l(r, \theta)$ alone, or in combination with the transmission signals $T(r, \theta)$, a distribution of scatter coefficients at elements of a matrix in the plane 4 which describes the internal structure of the irradiated body 5 can then be reconstructed. This will be elaborated hereinafter.

Obviously, the X-ray source 1 may also be replaced by a gamma radiation source or by a corpuscular radiation source, for example, a neutron radiation source. The detector device 7 is then chosen accordingly or its spectral sensitivity is adapted to the radiation of the relevant radiation source. The hollow-cylinder detectors 9 and 9' may be constructed, for example, as ionization detectors which consist each time of two concentric hollow cylinders 11 and 11' which are arranged one inside the other and wherebetween a pressurized ionizable gas is provided and wherebetween an electric voltage is applied.

The two hollow cylinders 9 and 9' may alternatively form an integral unit in order to increase the measurable scattered radiation. Thus, the scattered radiation which emerges from the body and which extends in the plane 4 is also measured. The primary radiation beam 3 then passes through an entrance and an exit window (not shown), the passage of the radiation beam 3 (obviously) not being impeded by the scattered radiation detector 7. During displacement or rotation of the X-ray source 1 or the primary radiation beam 3, the integral cylinder detector 7 should then be displaced and rotated accordingly, so that the primary radiation beam 3 can always pass through an entrance window and an exit window. The body 5 remains stationary.

In order to increase the part of the scattered radiation to be measured each time along a beam path $l(r, \theta)$, one of the end face of the hollow-cylinder detectors 9 and 9', which are remote from the plane 4 and which are situated on the outer side, can be covered with a detector plate, so that scattered radiation emitted in the direction of the cylinder axes 10 and 10' is also detected.

FIG. 2 shows a device in accordance with the invention which comprises two hollow-cylinder detectors 9 and 9' which enclose a body 5 arranged on a table 12 which is displaceable in three coordinate directions x, y, z. The radiation source 1 and the detector 8 are arranged one opposite the other on a displaceable support 13 which can be intermittently or continuously displaced in a direction in the plane 4 (x-y plane) by means of a gearwheel 15 which is driven by a motor 14 and a rack 16. The body 5 can thus be irradiated along a large number of parallel beam paths $l(r, \theta)$, situated in the plane 4, in an angular position $\theta$.

The support 13 is arranged, by means of bearings 17, between two bearing rails 18 and 18' which are rigidly connected to a supporting frame 19 which has a circular circumference and which is guided on guide rollers 20. The guide rollers 20 are supported by a stationary frame 200 (only diagrammatically shown). In order to change the direction $\theta$ of the radiation beam 3 in the plane 4 (see FIG. 1), the supporting frame 19 is rotated, by means of further motor 21 whose shaft accommodates a further gearwheel 22, around an axis which extends perpendicularly to the plane 4 (y-direction) and which may be, for example, the cylinder axis 10 and 10′. To this end, the further gearwheel 22 engages a gear ring 23 (only partly shown) which is situated on the circumference of the supporting frame 19. The hollow-cylinder detectors 9 and 9′ are not moved (relevant holders are not shown for the sake of clarity of the drawing).

The detector 8 which measures the transmitted radiation of the primary radiation beam 3 is electrically connected to an amplifier 24 which is electrically connected to a logarithmation unit 25 for amplification and logarithmation of the transmission signals T(r, θ) generated by the detector 8. The logarithmation unit 25 has connected to it an analog-to-digital converter 26 and thereto an electronic memory 27 is connected for the storage of the transmission signals T(r, θ) in digital form.

There is also provided an adding stage 28 which adds the analog output signals A(r, θ) and A′(r, θ) on the outputs of the hollow cylinder detectors 9 and 9′ in order to form a scatter signal S(r, θ). The scatter signals (r, θ) is amplified by an amplifier 29 and is digitized by the analog-to-digital converter 26. The scatter signals S(r, θ) thus converted are then also stored in the electronic memory 27. A computer 30 which is connected to the electronic memory 27 determines, on the basis of the scatter signals S(r, θ) alone or in combination with the transmission signals T(R, θ) obtained, a distribution of the scatter coefficient σ(m.n) at elements of a matrix situated in the plane 4 and having n rows and m columns of elements, which distribution of σ(m.n) is displayed on a display screen 31.

The computer 30 furthermore comprises a control system for control of the motors 14 and 21 for performing a displacement or rotation of the primary radiation beam 3 in the plane 4. The predetermined distance r or the angle θ of each beam path 1(r, θ) is stored in the electronic memory 27 in order to be available for the reconstruction at a later stage. The computer 30 is furthermore connected to an X-ray generator 32 for control of the X-ray tube 1.

FIG. 3 shows a process diagram of a method for determining a distribution of scatter coefficients σ from scatter signals S(r, θ), or scatter signals S(r, θ) and transmission signals T(r, θ), measured by means of the device in accordance with the invention.

When the energy of the primary radiation beam 3 is in the range of from approximately one hundred to a few hundreds of keV, the photoelectric absorption in the body 5 can be ignored. This can be done for radiation energies of from approximately 150 keV in human bodies, while in the case of examination of materials radiation energies of a few hundreds of keV are necessary.

In a first step (field 33) of the method, the hollow-cylinder detectors 9 and 9′ are used for recording for all beam paths (1(r, θ) the output signals A(r. θ) and A′(r, θ) which represent the intensity of the scattered radiation along a beam path 1(r, θ) of the primary radiation beam 3 and which are each time added for determining scattered signals S(r, θ).

Use is made of a previously selected distribution of scatter coefficients σ(m, n) on the elements of the matrix situated in the plane 4 (see FIG. 1) which approximates the internal structure of the body 5. This distribution may comprise, for example, equally large scatter coefficients σ(m, n) which are also stored in the memory 27, All beam paths 1(r, θ) are successively fetched (field 35, step two of the method) for calaulating scatter data $\overline{S}(r, \theta)$ for the individual beam paths 1(r, θ), the angular variation θ being effectively realized in steps of approximately 40°. The coordinates r and θ of the beam paths 1(r, θ) are already stored in the memory 27 for this purpose. During a next step, the scatter data $\overline{S}(r, \theta)$ are calculated in the computer 30 with the predetermined distribution σ(m, n) of the scatter coefficients (field 36). The scatter data $\overline{S}(r, \theta)$ are determined by using the formule:

$$\overline{S}(r, \theta) = So \int_1 \sigma \cdot K F \cdot dl \qquad (1)$$

The equation (1) provides a line integral of the scatter coefficient σ over the beam path 1, l being 1(r, θ). The scatter coefficient σ is multiplied by a factor K which describes the activation power of the hollow-cylinder detectors 9 and 9′. This factor K can be determined with high accuracy by the hollow-cylinder detectors 9 and 9′ by irradiating a test object along all beam paths 1(r, θ) by means of the primary radiation beam 3 and by measuring the scatter radiation (known) then occurring.

Furthermore, the scatter coefficient σ is multiplied by an attenuation factor F which describes the attenuation of the primary radiation beam 3 along the beam path 1(r, θ) as far as important element of the matrix. If the important element of the matrix on the path 1(r, θ) is denoted by the reference i, the attenuation factor F for the element i can be described as follows when the photoelectric absorption is neglected:

$$Fi = \exp \sum_{j=1}^{i-1} (-\sigma(j) \cdot \omega(j)) \qquad (2)$$

Therein, the scatter coefficients σ(j) of all elements j situated in the beam path 1(r, θ) before the relevant element i are summed, each time weighted with the expansion w(j) of the elements j in the direction of the beam path 1(r, θ). The expansion w(j) is then small in comparison with the characteristic changes of the internal structure of the body 5. The equation (1) furthermore comprises a factor So which indicates the known or predetermined output intensity of the X-ray source 1. The line integral (formule 1) can be converted into a sum, after which the scatter values $\overline{S}(r, \theta)$ can be calculated in a numerical manner for all beam paths 1(r, θ), taking into account the formula (2).

The next step (field 37) of the method comprises the comparison of the scatter values $\overline{S}(r, \theta)$ and the scatter signals S(r, θ) for each beam path 1(r, θ). Correction data α, where α = S(r, θ)/$\overline{S}$(r, θ), are calculated in a next step of the method (field 38) to correct all scatter coefficients σ of the associated beam path 1(r, θ) in accordance with $$\overline{\sigma} = \sigma \cdot \alpha \qquad (3)$$

The corrected scatter coefficients $\overline{\sigma}$ are stored in the memory 27.

After determination and processing (test in field 39) of the correction data for all beam paths (r, θ), it is tested (field 40) whether the difference (α) between the each time predetermined scatter coefficients σ and the corrected scatter coefficients $\overline{\sigma}$ is small enough to allow termination of the iteration process. If the deviation between the coefficients σ and σ is too large (|1 − α| > δ, δ being a small number to be chosen, the steps in the fields 34, 35, 36, 37, 38, 39 are executed again, the calculated scatter coefficients $\overline{\sigma}$ then being considered as being predetermined. If the routine loop 400 has been completed an adequate number of times, $|1-\alpha| \leq \delta$ and the scatter coefficients are sufficiently accurate.

Subsequently (field 41), the scatter coefficient distribution is displayed, for example, on the monitor 31.

If the photoelectric absorption in the body 5 cannot be neglected, for example, in the case of a radiation energy of the primary radiation beam 3 in the range of some tens of kilo-electronvolts, the attenuation factor Fi is described by the below formula (4) instead of the formule (2):

$$Fi = \exp \sum_{j=1}^{i-1} (-(\sigma(j) + K(j))\omega(j)) \qquad (4)$$

The addend k(j) therein indicates the part of the photoelectric absorption in the attenuation of the primary radiation beam 3. For calculating the scatter data $\overline{S}(r, \theta)$ (field 36), where also the attenuation of the radiation scattered in the body 5 is taken into account, a sum $\mu(j)$ of the scatter coefficient $\sigma(j)$ and the absorption coefficient k(j) must each time be known for a matrix element j. The sum $\mu(j)$, indicating the attenuation coefficient of a matrix element j, can be calculated in known manner by reconstruction of the attenuation coefficient distribution (see R. A. Brooks and G. di Ghiro, Phys. Med. Biol. 1976, Vol. 21, No. 5,689–732). However, during the measurement of the scatter signals S(r, $\theta$), also the transmission signals T(r, $\theta$) must then also be measured by measurement of the radiation of the primary radiation beam 3 transmitted by the body 5.

What is claimed is:

1. A device for determining the internal structure of a flat examination zone of a body comprising radiation means for emitting a primary radiation beam in a plane of the examination zone, said beam having a small cross-section, said radiation means being displaceable in said plane in a direction transversely of the direction of said primary radiation beam, and being rotatable about an axis extending perpendicular to said plane; detector means for generating measuring signals by detection of radiation emerging from the body, said detector means being free of said primary radiation beam and situated at least on one side of said plane to detect scattered radiation generated by said primary radiation beam so that scatter signals are obtained which are associated with the beam path, said detector means at least partly enclosing said body; calculating means for calculating a distribution of scatter coefficients in said plane from said scatter signals; and display means for displaying the internal structure, CHARACTERIZED IN THAT said detector means comprises two identical, hollow-cylinder detectors which together substantially completely envelop said body and which are arranged at a distance from each other in a mirror-symmetrical image with respect to said plane, said cylinder detectors having coincident cylinder axes extending transversely of said plane.

2. A device as claimed in claim 1, characterized in that said hollow-cylinder detectors are connected to an adder stage for addition of output signals.

3. A device as claimed in claim 1, characterized in that another detector situated in said plane is provided for detecting said primary radiation beam.

4. A device as claimed in claim 1, characterized in that said hollow-cylinder detectors form an integral unit, are rotatable about said cylinder axes, and displaceable in a direction perpendicular to said cylinder axes, said detectors being provided with apertures for passage of said primary radiation beam, said apertures being situated in said plane and radially opposite each other.

5. A device as claimed in claims 1 or 4, characterized in that one of the outer end faces of said hollow-cylinder detectors is covered with detector plates.

* * * * *